United States Patent [19]

Coughlin

[11] Patent Number: 4,617,283

[45] Date of Patent: Oct. 14, 1986

[54] CATALYST FOR CONVERTING SYNTHESIS GAS TO LIQUID MOTOR FUELS

[75] Inventor: Peter K. Coughlin, Yorktown Heights, N.Y.

[73] Assignee: Union Carbide Corporation, Danbury, Conn.

[21] Appl. No.: 625,371

[22] Filed: Jun. 27, 1984

[51] Int. Cl.$^4$ .................. B01J 29/02; B01J 29/06
[52] U.S. Cl. ............................... 502/66; 502/74; 502/214; 518/713
[58] Field of Search ............ 502/66, 74, 214; 518/713

[56] References Cited

U.S. PATENT DOCUMENTS

| | | | |
|---|---|---|---|
| 3,013,990 | 12/1961 | Breck et al. | 252/455 |
| 4,086,262 | 4/1978 | Chang et al. | 260/449.6 R |
| 4,146,503 | 3/1979 | Vogt et al. | 502/74 |
| 4,157,338 | 6/1979 | Haag et al. | 260/449 R |
| 4,172,843 | 10/1979 | Dwyer et al. | 260/449.6 R |
| 4,180,516 | 12/1979 | Chang et al. | 260/449 R |
| 4,190,558 | 2/1980 | Seitzer | 502/74 |
| 4,207,248 | 6/1980 | Butter et al. | 260/449.6 R |
| 4,279,830 | 7/1981 | Haag et al. | 518/700 |
| 4,304,871 | 12/1981 | Brennan et al. | 502/74 X |
| 4,340,503 | 7/1982 | Rao et al. | 252/459 |
| 4,440,871 | 4/1984 | Lok et al. | 502/214 |

FOREIGN PATENT DOCUMENTS

| | | | |
|---|---|---|---|
| 874373 | 2/1979 | Belgium . | |
| 45620 | 2/1982 | European Pat. Off. | 502/74 |
| 941349 | 11/1963 | United Kingdom | 502/74 |
| 2077754 | 6/1981 | United Kingdom . | |

OTHER PUBLICATIONS

"The Fischer-Tropsch Synthesis in the Liquid Phase'"—Catal. Rev.-Sci. Eng., 21(2), 225-274 (1980), Herbert Kolbel and Milos Ralek, pp. 225, 243-247.

Primary Examiner—Carl F. Dees
Attorney, Agent, or Firm—Gary L. Wamer

[57] ABSTRACT

The addition of an inert metal component, such as gold, silver or copper, to a Fischer-Tropsch catalyst comprising cobalt enables said catalyst to convert synthesis gas to liquid motor fuels at about 240°-370° C. with advantageously reduced selectivity of said cobalt for methane in said conversion. The catalyst composition can advantageously include a support component, such as a molecular sieve, co-catalyst/support component or a combination of such support components.

13 Claims, No Drawings

CATALYST FOR CONVERTING SYNTHESIS GAS TO LIQUID MOTOR FUELS

STATEMENT

The Government of the United States of America has rights to this invention pursuant to Contract No. DE-AC22-8IPC40077 awarded by the U.S. Department of Energy.

BACKGROUND OF THE INVENTION

1. Field of the Invention

The invention relates to the conversion of synthesis gas to hydrocarbons. More particularly, it relates to the conversion of such synthesis gas to $C_5+$ hydrocarbons suitable for use as liquid motor fuels.

2. Description of the Prior Art

It is well known in the art that synthesis gas, i.e., hydrogen and carbon monoxide, can be converted to hydrocarbons in the presence of a variety of transition metal catalysts. Thus, certain Group VIII metals, particularly iron, cobalt, ruthenium and nickel, are known to catalyze the conversion of CO and hydrogen, also referred to as syngas, to hydrocarbons. Such metals are commonly called Fischer-Tropsch catalysts. While the use of nickel preferentially produces methane upon conversion of syngas, the use of iron, cobalt and ruthenium tends to produce hydrocarbon mixtures consisting of hydrocarbons having a larger carbon number than methane, as determined by a number of analytical means including mass spectrographic analysis of individual components and the boiling point curve method. At higher reaction temperatures, all Fischer-Tropsch catalysts tend to produce gaseous hydrocarbons, and it is readily feasible to select processing conditions to produce methane as the principal product. At lower temperatures, and usually at higher pressures, however, iron, cobalt and ruthenium produce hydrocarbon mixtures consisting of larger hydrocarbons. These products usually contain very long straight-chain hydrocarbon molecules that tend to precipitate as wax. Such wax material, boiling well beyond the boiling range of motor fuels, typically constitutes a significant fraction of the product produced in such catalytic conversion operations. Fischer-Tropsch catalysts have not been advantageously employed in the production of liquid hydrocarbon motor fuels, therefore, instead commonly producing either principally gaseous hydrocarbons, on the one hand, or hydrocarbons containing an unacceptably large amount of wax on the other. In addition, the gasoline boiling hydrocarbon fraction that has been produced has an unacceptably low octane number.

In light of such circumstances, efforts have been made to improve the performance of Fischer-Tropsch catalysts for use in various desired syngas conversions. For example, the Breck et al. patent, U.S. Pat. No. 3,013,990, discloses the use of zeolitic molecular sieves containing a Fischer-Tropsch catalyst as improved catalyst compositions. Thus, Type A, X and Y molecular sieves loaded with iron or cobalt are shown to be suitable Fischer-Tropsch hydrocarbon synthesis catalysts, as for the production of methanol from syngas. Also with respect to the conversion of syngas, Fraenkel et al., U.S. Pat. No. 4,294,725, teach that zeolites A and Y loaded with cobalt, incorporated by ion exchange and reduced in-situ with cadmium, serve as useful catalysts of the Fischer-Tropsch type. Those skilled in the art will appreciate that such catalyst materials tend to be relatively expensive and, in any event, do not produce hydrocarbon products advantageous for use as liquid motor fuels.

Efforts have also been made to improve Fischer-Tropsch catalyst performance by preparing intimate mixtures of Fischer-Tropsch metals, such as iron, with an acidic crystalline aluminosilicate, such as ZSM-5. The Chang et al. patents, U.S. Pat. Nos. 4,086,262, and 4,096,163, disclose such catalyst compositions employed in the conversion of synthesis gas to hydrocarbon mixture useful in the manufacture of heating fuels, gasoline, aromatic hydrocarbons and chemical intermediates. When it is desired to convert syngas specifically to hydrocarbons boiling in the jet fuel+diesel oil boiling range, however, such an approach is not suitable, experiencing an effective limitation at $C_{10}$ carbon number as was the case using ZSM-5 in methanol conversion, as disclosed in the Owen et al. patent, U.S. Pat. No. 3,969,426.

While iron is the currently preferred Fischer-Tropsch catalyst component for use in syngas conversion operations, cobalt had originally been preferred because of its various desirable properties. Thus, cobalt has a higher level of catalytic activity in syngas conversion operations as well as a better selectivity to total motor fuels than is obtained using iron. One very objectional characteristic of cobalt, however, is the excessive amount of undesired methane that is produced when it is employed in syngas conversion operations, the level of methane production being considerably out-of-line with the level of other hydrocarbons produced and significantly diminishing the overall performance of said syngas conversion operations using cobalt as the Fischer-Tropsch catalyst.

It is nevertheless desirable in the art to develop improvements with respect to the use of cobalt as a Fischer-Tropsch catalyst for syngas conversion. More particularly, it is desirable to overcome the objectionable charactristics of cobalt by lowering its selectivity to methane during syngas conversion operations.

In prior art development work relating to various Fischer-Tropsch catalysts other than cobalt, the addition of copper and silver have been found to have varying effects on the selectivity of methane production. Thus, G. Bond and B. Turnham report in the *Journal of Catalysis* 1976, vol. 45, p. 128–136, that the addition of 50 mole % copper to a ruthenium catalyst causes the catalyst to lose significant activity and to become more selective for methanation and less selective for heavier hydrocarbon production, although one catalyst with only 3 mole % copper was found to follow the trend of the higher percentage copper catalysts, but to a lesser degree. On the other hand, D. Elliott and J. Lundsford report, in said *Journal of Catalysis,* 1979, vol. 57, p. 11–26, the observation of a decrease in methane selectivity upon addition of copper to a ruthenium-y zeolite composition, with this result attributed to a lower hydrogenolysis activity for the ruthenium-copper catalyst. Furthermore, J. Amelse, L. Schevarty and J. Butt report, again in said *Journal of Catalysis,* 1981, vol. 72, p. 95–110, that the use of an iron-copper Fischer-Tropsch catalyst containing about 25% copper based on the amount of iron therein produces more methane and less olefins than a corresponding iron catalyst without copper added thereto. The effects observed in such prior art work appear to have been dependent upon the nature of the particular Fischer-Tropsch metal component employed and upon the processing conditions employed.

It should be noted that such prior art activities relating to iron and ruthenium Fischer-Tropsch catalysts were carried out under processing conditions of high methane yield, but with varying, unpredictable results. Earlier prior art work using cobalt as the Fischer-Tropsch catalyst, however, was carried out under processing conditions of low methane selectivity, and no effect was seen with respect to said methane selectivity. Thus, the use of copper and silver in cobalt catalysts, as to reduce the reduction temperature of the cobalt, constitutes old work discussed in "The Fischer-Tropsch and Related Synthesis" by H. Storch, N. Golumbic and R. Anderson, John Wiley & Sons, N.Y. In addition, Fischer is known to have studied 9:1 and 1:1 cobalt:copper catalysts at atmospheric pressure and temperatures of about 190°–220° C. At these conditions, such catalysts gave quite saturated products and oxygenates. The copper was added to lower the reduction temperature of the cobalt because of equipment restrictions. No decrease in methane selectivity was observed in these experiments carried out for other purposes under conditions of low methane selectivity. Prior art experiments at I. G. Farben using a 1% silver in cobalt catalyst composition are also known to have been made, presumably at low temperature and with no noted reduction in methane yield although easier reduction and longer catalyst life were noted under th processing conditions employed. Once again, no advantageous reduction in the methane selectivity of the cobalt was either sought or observed, notably because the conditions employed for the purposes of such prior art work were such that the hydrogenolysis reaction likely leading to the production of methane as a secondary product were not employed.

Despite the variety of prior art activity referred to above, the disadvantageous characteristics of cobalt performance remain, precluding the use of cobalt as a Fischer-Tropsch catalyst, despite its outstanding activity and motor fuel selectivity when employed for syngas conversion. The desire also remains in the art, therefore, for the development of improvements enabling cobalt to be used for syngas conversion with lower selectivity for methane and a corresponding increase in selectivity for desired liquid hydrocarbon fuels.

It is an object of the invention, therefore, to provide an improved process and Fischer-Tropsch catalyst composition for the conversion of syngas to liquid motor fuels.

It is another object of the invention to provide a process and Fischer-Tropsch catalyst composition for lowering the selectivity of cobalt for methane.

With these and other objects in mind, the invention is hereinafter described in detail, the novel features thereof being particularly pointed out in the appended claims.

SUMMARY OF THE INVENTION

The methane selectivity of cobalt in syngas conversion operations is advantageously reduced by the addition to the cobalt of an inert metal component comprising gold, silver or copper. The conversion operations in which such reduction in methane selectivity is obtained are carried out at a reaction temperature of about 240°–370° C. The catalyst composition of the invention, employed under such operating conditions and supported by a molecular sieve co-catalyst/support components in particular embodiments, thus increases the selectivity of the cobalt to desired liquid hydrocarbon fuels.

DETAILED DESCRIPTION OF THE INVENTION

The objects of the invention are accomplished by the deactivation of methane production, which appears to constitute a secondary, hydrogenolysis reaction, by the addition of an inert metal component to the cobalt Fischer-Tropsch catalyst employed for syngas conversion to liquid motor fuels. The inert metal component, i.e. gold, silver or copper, accomplishes this desirable result without accompanying deactivation of the Fischer-Tropsch reactor itself. Such desirable lowering of the selectivity of cobalt for methane is effective at reaction temperatures of from about 240° C. to about 370° C. as further described below.

The synthesis gas, or syngas, treated in accordance with the practice of the invention generally comprises a mixture of hydrogen and carbon monoxide, usually together with smaller amounts of carbon dioxide, methane, nitrogen or other components as is well known in the art. Syngas is commonly produced by steam reforming of hydrocarbons or by the partial oxidation of coal and petroleum deposits, or by similar gasification of other carbonaceous fuels such as peat, wood and cellulosic waste materials. The hydrogen/carbon oxide volume ratio of such syngas is desirably in the range of from about 0.2/1 to about 6.0/1 prior to conversion to liquid motor fuels as herein disclosed and claimed. This ratio can be adjusted, if desired, by reaction of carbon monoxide with steam in the well-known water-gas shift reaction. If required, sulfur impurities can be removed from the syngas mixture by conventional means known in the art. It should also be noted that the syngas as described herein includes art-recognized equivalents, such as mixtures of carbon monoxide and steam, or of carbon dioxide and hydrogen, that can provide synthesis gas mixture by in-situ reaction under the operating conditions employed.

For the reasons indicated above, the invention is directed and specifically limited to the use of cobalt as the Fischer-Tropsch metal component of the syngas conversion catalyst composition herein disclosed and claimed. As a second component thereof, gold is advantageously employed to achieve the desired lowering of the methane selectivity of said cobalt. Copper and silver are other metals that can be employed, in place of gold, as the second component. Gold, silver and copper, or mixtures thereof, are herein referred to as the inert metal component conveniently mixed with the cobalt to form the Fischer-Tropsch catalyst composition of the invention.

Any convenient means may be employed to obtain the desired admixture of cobalt and said inert metal component. Thus, the inert metal component can be coprecipitated or otherwise intimately interdispersed with said cobalt, conveniently in the form of cobalt oxide, before or after the activation of said cobalt. It is generally preferred, however, to impregnate the cobalt metal component with a solution of a suitable salt of the inert metal component employed. Thus, the cobalt metal may conveniently be impregnated with a solution of auric acid ($HAuCl_4$), followed by the drying of the thus impregnated cobalt. Those skilled in the art will appreciate that various other salt solutions can be employed in other embodiments of the invention to achieve the desired admixing of cobalt with the inert metal component. For purposes of the invention, the inert metal component is employed in an amount within the range of from about 0.1 to about 50, preferably from about 0.5 to about 5, mole % based on the total amount of cobalt and said inert metal component present in the Fischer-Tropsch catalyst composition.

In the practice of the invention the desired lowering of the selectivity of cobalt for methane is effectively achieved in syngas conversion operations carried out, as indicated above, at a reaction temperature of from about 240° C. to about 370° C. It will be appreciated that the invention is applicable to processing conditions such that the cobalt catalyst, not modified as herein provided, would produce excess amounts of methane when employed for syngas conversion. At reaction temperatures below about 240° C., excess methane is not produced in any event, and the practice of the invention is not needed although the results obtainable at such lower temperature conditions are otherwise not suitable for the production of liquid motor fuels. At reaction temperature above about 370° C., on the other hand, the cobalt catalyst produces large amounts of methane in any event so that the addition of an inert metal component will not result in a significant and meaningful lowering of the selectivity of the catalyst for methane. The catalytic conversion reaction can be carried out, in the practice of the invention, at any desired pressure level, as at pressures of from about 0 to about 1,000 psig, typically at from about 0 to about 350 psig.

Prior to syngas conversion, the cobalt catalyst of the invention is reduced or activated by techniques employing hydrogen where or with other treating materials as known in the art. For example, the catalyst may be activated by first carbiding with a low $H_2/CO$ ratio gas, or with CO alone, at a temperature in the range of about 250°–320° C. and a pressure of from 0 psig to the synthesis gas pressure. The catalyst is then further treated with hydrogen under similar temperature and pressure conditions. Further information regarding the preparation and activation of Fischer-Tropsch catalysts is provided in the published art, as in CATAL.REV.-SCI.ENG.,21(2), 225–274 (1980), "The Fischer-Tropsch Synthesis in the Liquid Phase", by Herbert Kolbel and Miles Ralek, particularly pp. 242–247 thereof.

It will also be appreciated by those skilled in the art that the cobalt catalyst of the invention may also have a suitable promoter component incorporated therein. Potassium, sodium and thorium are examples of known promoters, with thorium being a preferred promoter for purposes of the syngas conversion operations of the invention. Thorium promotion can readily be accomplished by impregnating said cobalt catalyst or a metal-loaded, molecular sieve co-catalyst/support component with a thorium nitrate solution prior to drying and calcining. For example, a catalyst composition of the invention having cobalt precipitated on UHP-Y zeolite as hereafter described can be prepared by first precipitating the cobalt on the zeolite by the addition of aqueous ammonia to a boiling slurry of cobalt nitrate and said UHP-Y zeolite. After washing and drying the cobalt-loaded molecular sieve, said molecular sieve can be impregnated with a thorium nitrate solution, dried, pressed into pellets if desired, and air-calcined at 250° C. In another representative example, a physical mixture of cobalt and zeolite, promoted with thorium, is conveniently prepared from a solution of 0.05 g/ml of cobalt nitrate solution. Cobalt powder comprising $CoO \times H_2O$ is first precipitated by the addition of a stoichiometric amount of aqueous sodium carbonate. The resulting powder is collected, washed with hot distilled water, e.g. at about 95° C., and dried at 110° C. overnight. The cobalt powder is then impregnated with thorium nitrate solution and dried. Such thorium-promoted catalysts will typically contain about 15 wt. % $ThO_2$ although it will be appreciated that the concentration of thorium or other promoter employed will vary depending upon the promoter employed in any particular embodiment. In the latter example above, the thorium-promoted, precipitated cobalt powder can be ground slightly, mixed with an equal weight of UHP-Y zeolite, pressed into pellets, and air calcined at 250° C. for two hours to produce a metal and co-catalyst support composition comprising a physical mixture of said cobalt and UHP-Y zeolite containing about 20% cobalt by weight. Potassium-promoted catalysts will in general have a potassium concentration of from about 0.1 to about 5 wt. percent of $K_2O$, with sodium-promoted catalysts having a similar concentration range and thorium-promoted catalysts having such a concentration extended up to about 15%.

The Fischer-Tropsch catalyst composition of the invention, as indicated above, advantageously includes a support component for said cobalt and said inert metal component. In preferred embodiments, said support component comprises a molecular sieve co-catalyst/support component rather than an inert support component such as α-alumina. The presence of such a co-catalyst material facilitates the desired conversion of syngas to liquid motor fuels. In particularly preferred embodiments of the invention, the co-catalyst/support component comprises steam-stabilized, hydrophobic zeolite Y catalyst, sometimes referred to as ultrahydrophobic type zeolites, or simply as UHP-Y zeolites. The cobalt and the inert metal component may be positioned mainly within the large pores between the crystallites formed during the extrusion of the catalyst. It has also been found possible to place the cobalt and the metal component substantially within the crystallites of said UHP-Y zeolite or of aluminum extracted or acid extracted, UHP-Y zeolite as referred to below. The Y zeolites used in this invention are prepared by the steaming of the low-sodium forms of zeolite Y substantially as described in Belgian Pat. No. 874,373, issued Feb. 22, 1979. Such zeolites are organophilic zeolitic aluminosilicate compositions having a $SiO_2/Al_2O_3$ molar ratio equal to or greater than 4.5, and an essential X-ray powder diffraction pattern of zeolite Y. Furthermore, the zeolites have a crystallographic unit cell dimension, $a_o$, of less than 24.45 Angstroms, a sorptive capacity for water vapor at 25° C. and a $p/p_o$ value of 0.10 of less than 10.0 weight percent. In preferred compositions, said unit cell dimension of the catalyst is from 24.20 to 24.35 Angstroms. In addition, the water adsorption capacity at 25° C. and a $p/p_o$ value of 0.10 is desirably less than 6.0 or even 4.0 weight percent. More particularly, the $SiO_2/Al_2O_3$ molar ratio for certain embodiments is from 4.5 to 20.0. In a desirable embodiment in which the UHP-Y zeolite is acid extracted as discussed below, the $SiO_2/Al_2O_3$ molar ratio may be extended up to about 100 or more, as the alumina content of the zeolite is generally reduced to less than about 3 weight % or even to about 1 weight % or less in practical commercial applications.

For the determination of the sorptive capacity of the hydrophobic zeolite Y compositions for any particular adsorbate, e.g. water, the test zeolite sample is activated by perheating at 425° C. for 16 hours at a pressure of 5 micrometers of mercury in a conventional McBain apparatus. The temperature of the sample is thereafter adjusted to the desired value and contacted with the vapor of the test adsorbate at the desired pressure.

The hydrophobic zeolites suitable for purposes of the invention, as described above, have also been found especially suited for use as adsorbents in applications where it is desired to preferentially adsorb organic constituents from solutions or mixtures thereof with water. In the formation of synthesis gas by the distillation of coal for example, it is desirable, for environmental and economic reasons, to recover the relatively small portion of phenol present in the condensate fraction of principally water that is produced therein. For this purpose, the condensate can be contacted at ambient temperature with said hydrophobic zeolite that will selectively absorb the phenol from said condensate. Such zeolites have also been found highly suitable for use as base materials foor catalyst compositions having important commercial applications, e.g. in midbarrel hydrocracking catalyst compositions. The UHP-Y zeolites described in particular detail in the Belgian patent referred to above have been found active for the conversion of methanol to hydrocarbons ranging from methane to those boiling in the jet fuel and diesel oil boiling range up to about $C_{22}$ material.

The invention is hereinafter described with reference to specific comparative tests that are presented to illustrate the invention and the advantages thereof. These illustrative comparative tests should not be construed, however, as limiting the scope of the invention as set forth in the appended claims.

EXAMPLE I

This example is presented as a comparative reference and is based on the conversion of syngas using a thorium-promoted cobalt catalyst supported on a UHP-Y co-catalyst/support component without the admixture of an inert metal component with said cobalt as in the practice of the invention illustrated in Example II below. For purposes of this Example I, the cobalt metal component was prepared by precipitation upon the addition of a 10% excess of sodium carbonate solution to a stirred, room temperature aqueous solution of 400 g. of cobalt nitrate, $Co(NO_3)_2 \cdot 6H_2O$, in 1600 ml of water. The cobalt precipitate was washed with hot distilled water and dried at 110° C. overnight. It was then impregnated with thorium nitrate solution to provide a 15 wt. % thorium concentration, based on the weight of cobalt, on the precipitate, which was then dried at 110° C.

This thorium-promoted cobalt metal component was formed as ⅛" silica bonded extrudate containing 15% $Co/ThO_2$, 70% UHP-Y zeolite and 15% by wt. silica binder. The resulting extrudate was dried at 110° C. and calcined in air at 250° C. for two hours.

80 cc. of this catalyst was loaded into an internal recirculation reactor, in which it was heated, for cobalt activation, with hydrogen, at 300 psig, from room temperature up to 350° C., where it was held for 24 hours before cooling to 270° C. for treatment with 1:1 syngas. The syngas was fed to the reactor at a rate of about 300 GHSV, i.e., gas hourly space velocity, or volume of gas (at 0° C., 1 atm)/volume catalyst/hour. The conversion reaction was carried out at a pressure of about 300 psig and at a temperature of about 270° C. The results obtained in terms of the conversion of syngas, the primary product selectivity between hydrocarbons and $CO_2$, the hydrocarbon selectivity to the desirable $C+_5$ range and other pertinent product characterizations are as set forth below; including Table I, under the various operating conditions recited in the Table.

TABLE I

| Run | 1 | 2 | 3 | 4 | 5 |
|---|---|---|---|---|---|
| Hours on Stream | 19.5 | 115.5 | 139.5 | 163.5 | 187.5 |
| Temperature, °C. | 272 | 269 | 269 | 270 | 269 |
| Feed, cc/min. | 400 | 400 | 400 | 400 | 400 |
| Conversion, wt. % | | | | | |
| on CO | 62.86 | 44.21 | 39.12 | 40.43 | 38.31 |
| on $H_2$ | 89.40 | 72.07 | 66.43 | 67.26 | 65.97 |
| on (CO + $H_2$) | 75.66 | 58.36 | 52.78 | 53.81 | 52.12 |
| Product Selectivity, wt. % | | | | | |
| $CH_4$ | 14.67 | 19.66 | 23.12 | 22.63 | 24.15 |
| $C_2$-$C_4$ | 13.23 | 12.86 | 15.47 | 13.70 | 14.59 |
| $C_5$–420° F. | 50.41 | 42.22 | 38.71 | 41.04 | 39.90 |
| 420–700° F. | 19.19 | 20.35 | 16.74 | 16.65 | 15.78 |
| 700° F. End Point | 2.51 | 4.91 | 5.95 | 5.98 | 5.58 |
| $C_5$ End Point | 72.10 | 67.48 | 61.41 | 63.67 | 61.26 |
| Iso/Normal mole ratio | | | | | |
| $C_4$ | 0.2857 | 0.1226 | 0.1778 | 0.1370 | 0.1327 |
| $C_5$ | 0.5572 | 0.2546 | 0.2698 | 0.2540 | 0.2473 |
| $C_6$ | 0.9660 | 0.4117 | 0.4181 | 0.4006 | 0.3892 |
| Paraffin/Olefin ratio | | | | | |
| $C_3$ | 0.6912 | 1.4156 | 1.1943 | 1.2831 | 1.2776 |
| $C_4$ | 0.4206 | 0.7010 | 0.7044 | 0.6503 | 0.6289 |
| $C_5$ | 0.5004 | 0.7141 | 0.6954 | 0.6438 | 0.6146 |

Those skilled in the art will appreciated that the gasoline end point is about 420° F., while the diesel oil end point is about 700° F. It will also be appreciated that the 420°–700° F. hydrocarbon material comprises molecules with more carbon atoms than $C_{10}$ hydrocarbons up to about $C_{22}$ material. Hydrocarbon material in the $C_{22}$–$C_{28}$ range generally comprises heavy distillate material, with material above $C_{-28}$ generally comprising wax.

It will be seen that the cobalt catalyst shows an initial deactivation that tends to continue with time on stream. The level of methane production, which is relatively high initially, likewise increases with time on stream. While the selectivity to liquid hydrocarbons is relatively high, it will be appreciated that it could be higher in the event that the methane selectivity were reduced. The quality of the condensed product obtained was found not to be entirely satisfactory, since it contained some solid along with liquid hydrocarbons. The total condensed product obtained was distilled and fractioned into gasoline (initial boiling point—420° F.), jet fuel (300°–550° F.) and diesel oil (300°–700° F.) fractions. Upon FIA, i.e. Florescence Indicator Absorption, analysis, the gasoline fraction was found to contain 36.4% olefins, and the jet fraction was found to contain 31.6% olefins but to have a pour point, i.e. the lowest temperature at which the liquid flows, of 0° F. The diesel fraction had a pour point of 50° F.

EXAMPLE II

In this comparative example illustrating the practice of the invention, the catalyst composition was prepared as in Example I above except that the thorium-promoted cobalt component was impregnated with sufficient chloroauric acid solution, prior to formulation into the extrudate, to obtain approximately 2% gold deposited on the cobalt oxide. The metal component was dried and then formulated into an extrudate as in said Example I. The catalyst loading, pretreatment and testing for syngas conversion were also essentially as set forth in Example I. The results obtained are set forth in Table II below.

TABLE II

| Run | 1 | 2 | 3 | 4 | 5 |
|---|---|---|---|---|---|
| Hours on Stream | 70.9 | 118.9 | 143.4 | 168.8 | 214.5 |
| Temperature, °C. | 270 | 269 | 269 | 268 | 269 |
| Feed, cc/min. | 400 | 400 | 400 | 400 | 400 |
| Conversion, wt. % | | | | | |
| on CO | 38.68 | 35.34 | 34.85 | 34.69 | 36.25 |
| on $H_2$ | 77.62 | 73.11 | 72.54 | 71.71 | 71.93 |
| on (CO + $H_2$) | 58.27 | 53.90 | 53.35 | 53.00 | 54.04 |
| Product Selectivity, wt. % | | | | | |
| $CH_4$ | 14.14 | 17.70 | 18.58 | 18.17 | 17.78 |
| $C_2$-$C_4$ | 12.80 | 13.85 | 13.95 | 14.97 | 13.08 |
| $C_5$-420° F. | 46.86 | 42.37 | 40.23 | 40.29 | 38.95 |
| 420° F.–700° F. | 21.70 | 21.59 | 21.62 | 18.64 | 23.96 |
| 700° F.- end point | 4.49 | 4.50 | 5.63 | 7.92 | 6.23 |
| $C_5$- end point | 73.06 | 68.45 | 67.47 | 66.86 | 69.14 |
| Iso/normal mole ratio | | | | | |
| $C_4$ | 0.1913 | 0.1272 | 0.1092 | 0.1471 | 0.1122 |
| $C_5$ | 0.3226 | 0.2085 | 0.1966 | 0.1678 | 0.1561 |
| $C_6$ | 1.2078 | 1.0447 | 0.9495 | 1.0217 | 1.0011 |
| Paraffin/Olefin ratio | | | | | |
| $C_3$ | 0.6638 | 0.6912 | 0.6770 | 0.6824 | 0.7207 |
| $C_4$ | 0.4198 | 0.4097 | 0.4061 | 0.4937 | 0.4593 |
| $C_5$ | 0.6082 | 0.6016 | 0.5933 | 0.4282 | 0.5622 |

It will be seen from the results of Example II as compared with those of Example I, the activity of the reference catalyst and of the catalyst of the invention are comparable at similar run times on stream. However, the selectivity to methane of the catalyst of the invention is and remains lower than that of the corresponding reference catalyst without gold added thereto. The desirably lower methane selectivity of the catalyst of the invention leads, in turn, to better selectivity for both gasoline and diesel oil, the desired products of the syngas conversion operation.

The admixing of the inert metal component, i.e. gold in the subject example, is also found to lower the paraffin/olefin ratio of the $C_3$, $C_4$ and $C_5$ hydrocarbons produced. The liquid fractions obtained, i.e. gasoline, jet and diesel oil fractions, are also more olefinic than in Example I. This is especially desirable in catalyst compositions containing a molecular sieve material, since the molecular sieve can act upon olefins much easier than it can act upon paraffins, leading to the production of more desirable liquid motor fuel materials. The gasoline fraction in Example II was found to contain 46% olefins, while the jet fraction contained 45% olefins. The pour point of the jet material is −5° F., and the diesel oil has a pour point of 50° F. While this combination is barely improved from the results of Example I, the condensed liquid product of Example II advantageously contains no solid material therein.

Those skilled in the art will appreciate that various changes and modifications can be made in the details of the invention without departing from the scope of the invention as set forth in the appended claims. Thus, as noted above, the desired deactivation of methane production, by the addition of gold, silver or copper as an inert metal component to a cobalt metal component can be facilitated by the use of a modified UHP-Y co-catalyst/support component or by the use of other such desirable support components. For example, he UHP-Y zeolite referred to above can be employed in aluminum-extracted form. Furthermore, the cobalt and inert metal particles can advantageously be positioned substantially within the crystallites of the UHP-Y zeolite or of aluminum-extracted UHP-Y zeolite and not merely within the large pores between the crystallites formed during extrusion of the catalyst, thus enhancing catalyst stability. For such uses with UHP-Y, and in general when a co-catalyst support component is used, the cobalt metal component will be employed in an amount within the range of from about 1% to about 25% by weight based on the overall weight of the catalyst composition, with cobalt concentrations of from about 5% to about 15% being generally preferred in most applications. When a co-catalyst/support component is not employed, from about 1% to about 100% cobalt by weight is useful, based on the total weight of cobalt, inert metal and possibly other additives with about 5% to about 50% cobalt being preferred.

For purposes of achieving the aluminum-extracted form of said UHP-Y zeolite, the zeolite is conveniently acid washed or extracted essentially by the process as described in the Eberly patent, U.S. Pat. No. 3,591,488, to remove a large portion of the alumina from its pores prior to treatment to incorporate the metal component therein. By employing a suitable cobalt-containing liquid, such as cobalt carbonyl or a solution of cobalt nitrate or other cobalt salt, the metal can be positioned within the crystals, the adsorbed therein to form a co-catalyst/support composition highly advantageous for purposes of the invention. In an illustrative example, UHP-Y molecular sieve zeolite was refluxed in a 13% slurry of said sieve in 3.75M hydrochloric acid for three hours. The slurry was then cooled, and the supernatent was decanted therefrom. The remaining slurry was diluted in half, filtered and washed chloride-free with 0.001M nitric acid. The slurry was then washed with distilled water, dried at 110° C. for 16 hours and then at 250° C. for 16 hours and at 500° C. for an additional two hours and bottled at 400° C. The thus-treated material comprises acid-extracted substantially alumina-free, or aluminum extracted, UHP-Y zeolite.

In preparing the catalyst composition of the invention in embodiments including a co-catalyst/support component, the cobalt metal component, promoted and admixed with said inert metal component, can be physically mixed with the co-catalyst/support component, as in the examples above, or can be precipitated on or pore filled in said co-catalyst/support component. For purposes of positioning the cobalt within the crystals of UHP-Y zeolite or the aluminum-extracted form thereof, a suitable cobalt solution can be loaded into the zeolite by impregnation followed by heating or treatment with base. Addition of the inert metal and/or of thorium or other promoter can be accomplished either during cobalt impregnation or separately thereafter.

Another advantageous co-catalyst/support component for purposes of the invention is a crystalline, microporous SAPO silicoaluminophosphate, non-zeolite molecular sieve catalyst. Such catalyst materials, known as SAPOs and available at Union Carbide Corporation, are described in U.S. Pat. No. 4,440,871, issued Apr. 3, 1984. Individual members of the SAPO class are designated as SAPO-5, SAPO-11, SAPO-17, SAPO-20, SAPO-31, SAPO-34 and the like as disclosed in said patent application. SAPO-11 and SAPO-31 are generally preferred for purposes of the invention, although it will be appreciated that other SAPOs, or combinations thereof alone or with other molecular sieves, may also be employed. It is, for example, within the scope of the invention to employ a steam-stablized, hydrophobic zeolite Y, i.e. UHP-Y, as an additional co-catalyst/support component in addition to said SAPO material. In particular embodiments, the cobalt and said inert metal component admixed therewith are positioned inside said zeolite Y component, as inside the crystallites of said UHP-Y, or of the aluminum-extracted form thereof, with the thus-loaded UHP-Y co-catalyst/support component being used together with said SAPO or other suitable co-catalyst/support component. It will be understood that such specific embodiments are intended to achieve the desired reduction in methane selectivity by the use, under the syngas conversion conditions disclosed and claimed herein, of catalyst compositions that also have desirable stability and catalytic activity favorable to the production of the desired liquid motor fuels. In such specific embodiments and more generally, the invention utilizes a modification of cobalt not previously appreciated, in the context of syngas conversion and of excess methane selectivity therein, to achieve a significant advance in the production of motor fuels from such syngas. The invention thus enables the methane formation reaction to be deactivated to an appreciable extent, thereby overcoming the principal disadvantage of the otherwise preferred use of cobalt for syngas conversion. The invention thus represents an important advance in the continuing desire and need for improvements in the ability of the art to provide the liquid motor fuel requirements of industrial societies.

I claim:

1. A synthesis gas conversion catalyst composition adapted for the enhanced conversion of synthesis gas comprising carbon monoxide and hydrogen to $C_{+5}$ hydrocarbon mixtures having enhanced suitability for use as liquid motor fuels comprising:
   (a) a Fischer-Tropsch catalyst component comprising cobalt; and
   (b) a gold metal component and present in an amount within the range of from about 0.1 to about 50 mole % based on the total amount of cobalt and gold in said composition, whereby the selectivity of cobalt for methane in said synthesis gas conversion is desirably lowered by said gold, increasing the selectivity of said cobalt to desired liquid hydrocarbon fuels.

2. The composition of claim 1 in which said cobalt is promoted with thorium.

3. The composition of claim 1 in which said cobalt is promoted with potassium.

4. The composition of claim 1 in which said cobalt is promoted with sodium.

5. The composition of claim 2 in which said inert metal component comprises gold present in an amount within the range of from about 0.5 to about 5 mole % based on the amount of cobalt in said composition.

6. The composition of claim 1 and including a molecular sieve co-catalyst/support component for said cobalt.

7. The composition of claim 6 in which said co-catalyst/support component comprises a steam-stabilized, hydrophobic zeolite Y catalyst.

8. The composition of claim 7 in which the said co-catalyst/support component comprises said zeolite Y in aluminum-extracted form, said cobalt being positioned substanially within the crystallites of said acid-extracted zeolite.

9. The composition of claim 6 in which said co-catalyst/support component for said cobalt comprises a crystalline, microporous silicoaluminophosphate, non-zeolite molecular sieve catalyst.

10. The composition of claim 9 and including a steam stablizied, hydrophobic zeolite Y additional co-catalyst/support component.

11. The composition of claim 10 in which said zeolite Y is in aluminum-extracted form, said cobalt being positioned substantially within the crystallites of said acid-extracted zeolite.

12. The composition of claim 11 in which said catalyst comprises SAPO-11.

13. The composition of claim 11 in which said catalyst comprises SAPO-31.

* * * * *